(12) United States Patent
Anderson et al.

(10) Patent No.: US 8,313,519 B2
(45) Date of Patent: Nov. 20, 2012

(54) MULTIFUNCTION WARMING DEVICE WITH AN UPPER BODY CONVECTIVE APPARATUS

(75) Inventors: Thomas P. Anderson, Savage, MN (US); Shad N. Lindrud, Albertville, MN (US); Gary R. Maharaj, Eden Prairie, MN (US); Carol J. Panser, St. Louis Park, MN (US); Mark J. Scott, Maple Grove, MN (US); Teryl L. Woodwick Sides, Maple Grove, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 181 days.

(21) Appl. No.: 12/927,800

(22) Filed: Nov. 24, 2010

(65) Prior Publication Data

US 2011/0077724 A1    Mar. 31, 2011

Related U.S. Application Data

(62) Division of application No. 11/583,481, filed on Oct. 19, 2006, now Pat. No. 7,857,841.

(60) Provisional application No. 60/729,000, filed on Oct. 20, 2005, provisional application No. 60/835,602, filed on Aug. 4, 2006.

(51) Int. Cl.
*A61F 7/00* (2006.01)
(52) U.S. Cl. .................................. 607/107; 607/104
(58) Field of Classification Search .................. 607/104, 607/107, 114; 2/69, 114
See application file for complete search history.

(56) References Cited

U.S. PATENT DOCUMENTS

| | | | |
|---|---|---|---|
| 2,512,559 A | 9/1950 | Williams | 5/347 |
| 2,573,414 A | 10/1951 | Dunn | 128/144 |
| 2,826,758 A | 3/1958 | Kahn | 2/61 |
| 3,468,299 A | 9/1969 | D'Amato | 126/204 |
| 3,610,323 A | 10/1971 | Troyer | 165/46 |
| 3,757,366 A | 9/1973 | Sacher | 5/347 |
| 3,855,635 A | 12/1974 | Ramirez | 2/114 |
| 3,911,499 A | 10/1975 | Benevento et al. | 2/114 |
| 3,950,789 A | 4/1976 | Konz et al. | 2/93 |
| 4,055,173 A | 10/1977 | Knab | 128/139 |

(Continued)

FOREIGN PATENT DOCUMENTS

FR        821150        11/1937

(Continued)

OTHER PUBLICATIONS

P.O. Fanger, Thermal Comfort: Analysis and Applications in Environmental Engineering, Danish Technical Press, 1970, pp. 5-67.

(Continued)

*Primary Examiner* — Roy Gibson
(74) *Attorney, Agent, or Firm* — Adam M. Bramwell; Terrance A. Meador

(57) ABSTRACT

A multifunction warming device includes a clinical garment having an inside surface supporting a convective apparatus disposed to provide therapeutic warming of a patient's upper body during surgery. The warming device includes a clinical garment with an elongate convective apparatus supported on the inside of the garment, transversely to the garment, and running between its sleeves. The positioning of the convective apparatus in the clinical garment locates it against the chest of a patient wearing the garment and permits it to be deployed and used on the patient's upper body during and after surgery without removal of the clinical garment from the patient or removal of the convective apparatus from the clinical garment.

7 Claims, 9 Drawing Sheets

U.S. PATENT DOCUMENTS

| | | | | |
|---|---|---|---|---|
| 4,146,933 A | 4/1979 | Jenkins et al. | | 2/2 |
| 4,369,528 A | 1/1983 | Vest et al. | | 2/69 |
| 4,494,248 A | 1/1985 | Holder | | 2/69 |
| 4,524,463 A | 6/1985 | Ogden | | 2/105 |
| 4,558,468 A | 12/1985 | Landry et al. | | 2/51 |
| 4,578,825 A | 4/1986 | Vote | | 2/114 |
| 4,587,671 A | 5/1986 | Rodriguez et al. | | 2/69 |
| 4,651,727 A | 3/1987 | Howorth | | 128/201.3 |
| 4,653,120 A | 3/1987 | Leaf | | 2/114 |
| 4,696,066 A | 9/1987 | Ball et al. | | 2/272 |
| 4,718,124 A | 1/1988 | Sawicki et al. | | 2/114 |
| 4,787,101 A | 11/1988 | Feinberg | | 2/105 |
| 4,914,752 A | 4/1990 | Hinson et al. | | 2/2 |
| 4,964,282 A | 10/1990 | Wagner | | 62/259.3 |
| 5,062,424 A | 11/1991 | Hooker | | |
| 5,190,031 A | 3/1993 | Guibert et al. | | 128/399 |
| 5,255,390 A | 10/1993 | Gross et al. | | |
| 5,304,213 A | 4/1994 | Berke et al. | | 607/104 |
| 5,360,439 A | 11/1994 | Dickerhoff et al. | | 607/104 |
| 5,367,710 A | 11/1994 | Karmin | | 2/114 |
| 5,411,541 A | 5/1995 | Bell et al. | | 607/104 |
| 5,443,488 A | 8/1995 | Namenmye et al. | | 607/104 |
| 5,572,742 A | 11/1996 | McFadden | | 2/114 |
| 5,575,006 A | 11/1996 | Wolfe | | 2/114 |
| 5,611,087 A | 3/1997 | Adkins | | 2/114 |
| 5,620,482 A | 4/1997 | Augustine et al. | | 607/104 |
| 5,697,963 A | 12/1997 | Augustine | | 607/108 |
| 5,733,318 A | 3/1998 | Augustine | | 607/104 |
| 5,749,109 A | 5/1998 | Kappel | | 5/423 |
| 5,785,716 A | 7/1998 | Bayron | | 607/108 |
| 5,891,187 A | 4/1999 | Winthrop et al. | | 607/96 |
| 5,946,722 A | 9/1999 | Trautmann | | 2/83 |
| 5,970,519 A | 10/1999 | Weber | | 2/81 |
| 5,974,605 A | 11/1999 | Dickerhoff et al. | | 5/421 |
| 6,049,907 A | 4/2000 | Palomo | | 2/51 |
| 6,154,883 A | 12/2000 | Spann et al. | | 2/69 |
| 6,156,058 A | 12/2000 | Kappel et al. | | 607/107 |
| 6,203,567 B1 | 3/2001 | Augustine | | 607/104 |
| 6,216,270 B1 | 4/2001 | Moquin et al. | | 2/69 |
| 6,235,659 B1 | 5/2001 | McAmish et al. | | 442/79 |
| 6,378,136 B2 | 4/2002 | Matsushita | | 2/114 |
| 6,484,321 B1 | 11/2002 | Shamam | | 2/114 |
| 6,511,501 B1 | 1/2003 | Augustine et al. | | 607/96 |
| 6,524,332 B1 | 2/2003 | Augustine et al. | | 607/107 |
| 6,551,347 B1 | 4/2003 | Elkins | | 607/104 |
| 6,571,574 B1 | 6/2003 | Blackstone | | 62/420 |
| 6,596,019 B2 | 7/2003 | Turner et al. | | 607/108 |
| 6,647,552 B1 | 11/2003 | Hogan | | 2/114 |
| 6,694,522 B1 | 2/2004 | Neal | | 2/114 |
| 6,792,622 B2 | 9/2004 | Graves | | 2/114 |
| 6,799,332 B2 | 10/2004 | Hatton | | 2/114 |
| 6,820,622 B1 | 11/2004 | Teves et al. | | 128/849 |
| 6,851,125 B2 | 2/2005 | Fujikawa et al. | | 2/51 |
| 6,876,884 B2 | 4/2005 | Hansen et al. | | 607/96 |
| 7,001,416 B2 | 2/2006 | Augustine et al. | | 607/104 |
| 7,226,454 B2 | 6/2007 | Albrecht et al. | | 607/104 |
| 7,276,076 B2 | 10/2007 | Bieberich | | 607/108 |
| 7,364,584 B2 | 4/2008 | Anderson | | 607/108 |
| 7,470,280 B2 | 12/2008 | Bieberich | | 607/104 |
| 2003/0126668 A1 | 7/2003 | Scroggins | | 2/114 |
| 2005/0015127 A1 | 1/2005 | Bieberich | | 607/104 |
| 2005/0143796 A1 | 6/2005 | Augustine et al. | | 607/104 |
| 2006/0047332 A1 | 3/2006 | Malmberg et al. | | 607/104 |
| 2006/0122671 A1 | 6/2006 | Albrecht et al. | | 607/104 |
| 2006/0122672 A1 | 6/2006 | Anderson | | 607/104 |
| 2006/0147320 A1 | 7/2006 | Hansen et al. | | 417/313 |
| 2006/0184216 A1 | 8/2006 | Van Duren | | 607/104 |
| 2006/0184217 A1 | 8/2006 | Van Duren | | 607/104 |
| 2006/0184218 A1 | 8/2006 | Bieberich | | 607/104 |
| 2006/0259104 A1 | 11/2006 | Panser | | 607/104 |
| 2007/0093882 A1 | 4/2007 | Anderson et al. | | 607/104 |
| 2007/0093883 A1 | 4/2007 | Anderson et al. | | 607/104 |
| 2007/0093884 A1 | 4/2007 | Anderson et al. | | 607/104 |
| 2007/0093885 A1 | 4/2007 | Anderson et al. | | 607/104 |
| 2007/0239239 A1 | 10/2007 | Albrecht et al. | | 607/96 |
| 2008/0027521 A1 | 1/2008 | Bieberich | | 607/96 |
| 2008/0027522 A1 | 1/2008 | Bieberich | | 607/96 |
| 2008/0125840 A1 | 5/2008 | Anderson | | 607/96 |
| 2008/0177361 A1 | 7/2008 | Anderson | | 607/108 |
| 2009/0062891 A1 | 3/2009 | Bieberich | | 607/104 |
| 2009/0149931 A9 | 6/2009 | Anderson | | 607/104 |
| 2009/0228083 A1 | 9/2009 | Anderson et al. | | 607/107 |

FOREIGN PATENT DOCUMENTS

| | | |
|---|---|---|
| GB | 475811 | 11/1937 |
| GB | 1 462 033 | 1/1997 |
| SE | 525 415 C2 | 2/2005 |
| WO | 97/14381 A1 | 4/1997 |
| WO | WO 98/48652 A1 | 11/1998 |
| WO | WO 00/62726 A1 | 10/2000 |
| WO | WO 03/086500 A2 | 10/2003 |
| WO | WO 03/106897 A3 | 12/2003 |
| WO | WO 2004/004500 A1 | 1/2004 |
| WO | WO 2006/020170 A1 | 2/2006 |
| WO | WO 2006/062910 A1 | 6/2006 |
| WO | WO 2006/063027 A1 | 6/2006 |
| WO | WO 2006/086587 A1 | 8/2006 |
| WO | WO 2007/047917 A1 | 4/2007 |
| WO | WO 2008/013603 A1 | 1/2008 |
| WO | WO 2008/091486 A2 | 7/2008 |

OTHER PUBLICATIONS

C.B. Mahony & J. Odom, Maintaining intraoperative normothermia: A meta-analysis of outcomes with costs. *AANA Journal*. Apr. 1999. v. 67, No. 2:155-164.
Porta-Chill—The Portable Air-Chiller—Brochure, http://www.portachil.com/, 12/03/22.
International Search Report & Written Opinion in PCT/US2005/025355, mailed Dec. 1, 2005.
International Search Report & Written Opinion in PCT/US2005/043968, mailed Apr. 19, 2006.
International Search Report & Written Opinion in PCT/US2005/044214, mailed Apr. 19, 2006.
International Search Report & Written Opinion in PCT/US2006/004644, mailed Dec. 18, 2006.
International Search Report & Written Opinion in PCT/US2006/041028, mailed Feb. 20, 2007.
International Search Report & Written Opinion in PCT/US2007/013073, mailed Nov. 9, 2007.
International Search Report & Written Opinion in PCT/US2008/000141, mailed Nov. 11, 2008.
EPO Examination Report mailed Oct. 24, 2006, in EPO3719690.4, EP Regional Phase of PCT/US2003/11128 (published as WO/2003/086500).
EPO Examination Report mailed Dec. 17, 2007, in EPO3719690.4, EP Regional Phase of PCT/US2003/11128 (published as WO/2003/086500).
EPO Examination Report mailed Jan. 8, 2008, in EP05853005.6, EP Regional Phase of PCT/US2005/043968 (published as WO/2006/062910).
EPO Examination Report mailed Sep. 2, 2008, in EP05789978.3, EP Regional Phase of PCT/US2005/025355 (published as WO/2006/020170).
EPO Examination Report mailed Jan. 23, 2009, in EP05853202.9, EP Regional Phase of PCT/US2005/044214 (published as WO/2006/063027).
EPO Examination Report mailed Apr. 24, 2009, in EP06826351.6, EP Regional Phase of PCT/US2006/041028 (published as WO/2007/047917).
EPO Examination Report mailed Jun. 22, 2009, in EP05853202.9, EP Regional Phase of PCT/US2005/044214 (published as WO/2006/063027).
Response to Examination Report in EP06826351.6, submitted Aug. 20, 2010.
EPO Examination Report mailed Sep. 3, 2009 in EP 07795671.2, EP Regional Phase of PCT/US2007/013073 (published as WO/2008/013603).
EPO Examination Report mailed Sep. 29, 2009, in EP06720577.3, EP Regional Phase of PCT/US2006/004644 (published as WO/2006/086587).
EPO Examination Report mailed Apr. 14, 2010 in EP06826351.6, EP Regional Phase of PCT/US2006/041028 (published as WO/2007/047917).

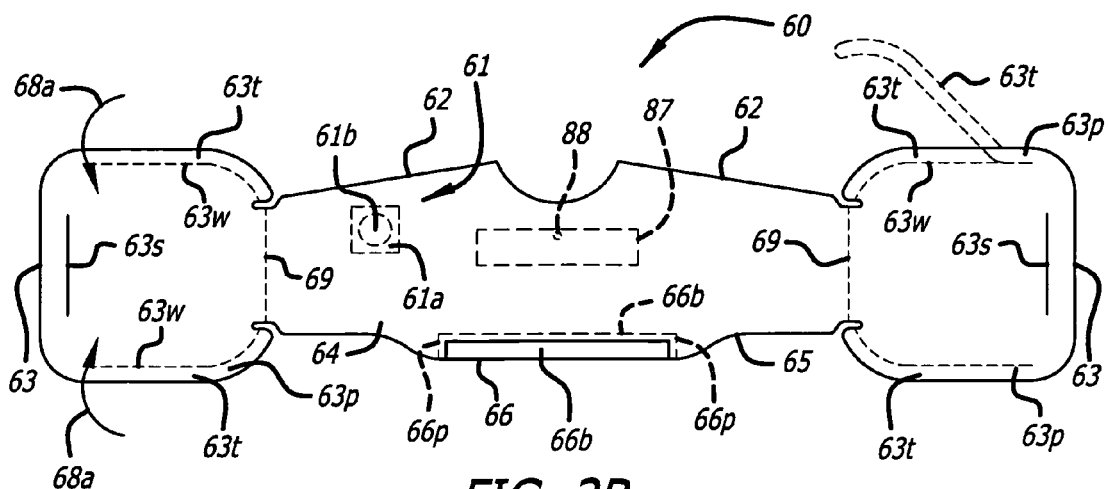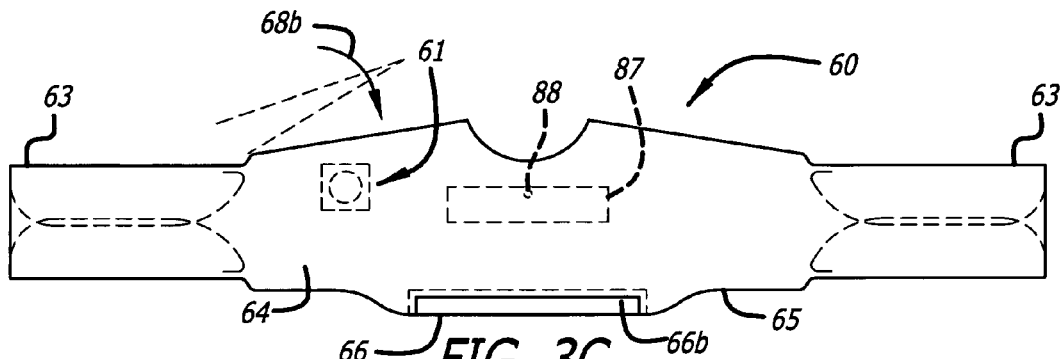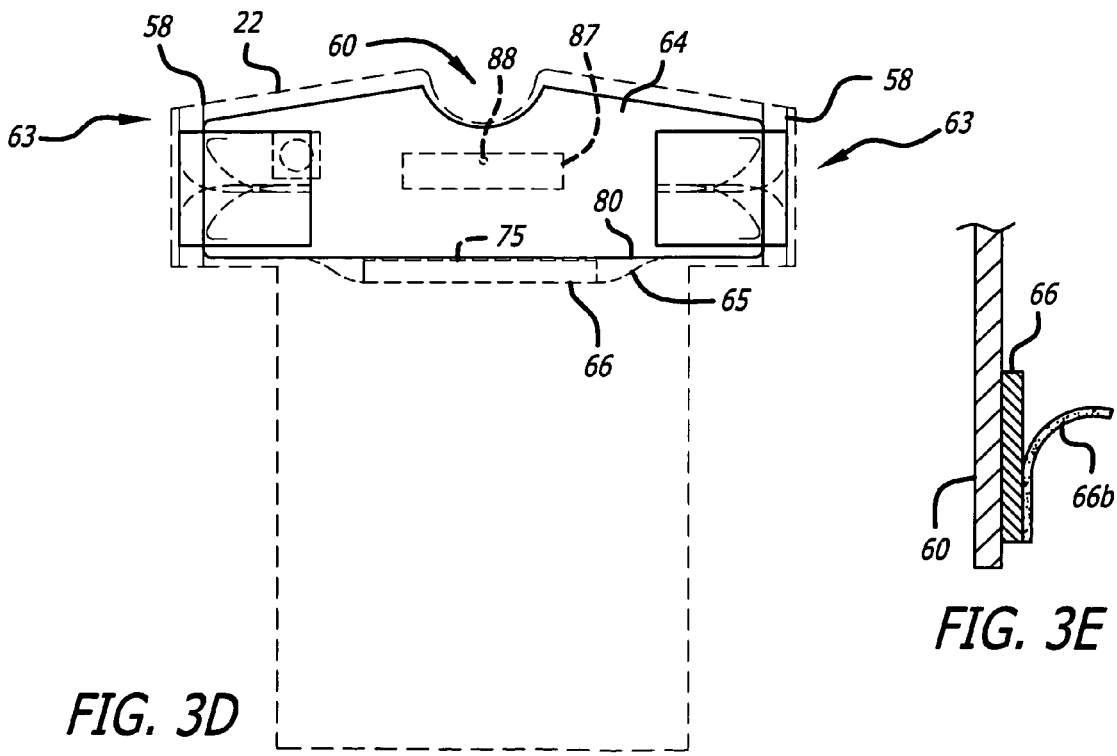

MULTIFUNCTION WARMING DEVICE WITH AN UPPER BODY CONVECTIVE APPARATUS

RELATED APPLICATIONS

This application is a divisional of U.S. patent application Ser. No. 11/583,481, filed Oct. 19, 2006, which claims priority to U.S. Provisional patent application 60/729,000, filed Oct. 20, 2005 and to U.S. Provisional patent application 60/835,602, filed Aug. 4, 2006.

This application contains subject matter related to the subject matter of the following patent applications, all commonly owned herewith and all incorporated by reference:

Patent Cooperation Treaty (PCT) Application No. PCT/US03/011128, filed Apr. 10, 2003, entitled "Patient Comfort Apparatus and System", and published on Oct. 23, 2003 under Publication No. WO 2003/086500;

Patent Cooperation Treaty (PCT) Application No. PCT/US05/025355, filed Jul. 18, 2005, entitled "Perioperative Warming Device", and published on Feb. 23, 2006 under Publication No. WO 2006/020170;

Patent Cooperation Treaty (PCT) Application No. PCT/US05/043968, filed Dec. 6, 2005, entitled "Warming Device with Varied Permeability", and published on Jun. 15, 2006 under Publication No. WO 2006/062910;

Patent Cooperation Treaty (PCT) Application No. PCT/US05/044214, filed Dec. 6, 2005, entitled "Warming Device", and published on Jun. 15, 2006 under Publication No. WO 2006/063027;

Patent Cooperation Treaty (PCT) Application No. PCT/US06/004644, filed Feb. 9, 2006, entitled "Warming Device for Perioperative Use", and published on Aug. 17, 2006 under Publication No. WO 2006/086587;

U.S. patent application Ser. No. 10/411,865, filed Apr. 10, 2003, entitled "Patient Comfort Apparatus and System" and published on Oct. 16, 2003 under Publication No. US 2003/0195596 and issued on Feb. 21, 2006 under U.S. Pat. No. 7,001,416;

U.S. patent application Ser. No. 10/508,319, filed Sep. 20, 2004, entitled "Patient Comfort Apparatus and System" and published on Jun. 30, 2005 under Publication No. US 2005/0143796;

U.S. patent application Ser. No. 11/005,883, filed Dec. 7, 2004, entitled "Warming Device with Varied Permeability" and published on Jun. 8, 2006 under Publication No. US 2006/0122671, now U.S. Pat. No. 7,226,454;

U.S. patent application Ser. No. 11/006,491, filed Dec. 7, 2004, entitled "Warming Device" and published on Jun. 8, 2006 under Publication No. US 2006/0122672;

U.S. patent application Ser. No. 11/057,396, filed Feb. 11, 2005, entitled "Perioperative Warming Device", and published on Aug. 17, 2006 under Publication No. US 2006/0184215, now U.S. Pat. No. 7,276,076;

U.S. patent application Ser. No. 11/057,403, filed Feb. 11, 2005, entitled "Warming Device for Perioperative Use", and published on Aug. 17, 2006 under Publication No. US 2006/0184217;

U.S. patent application Ser. No. 11/057,404, filed Feb. 11, 2005, entitled "Clinical Garment for Comfort Warming and Prewarming", and published on Aug. 17, 2006 under Publication No. US 2006/0184218; and, U.S. patent application Ser. No. 11/363,136, filed Feb. 27, 2006, entitled "Forced Air Warming Unit" and published on Jul. 6, 2006 under Publication No. US2006/0147320.

This application also contains subject matter related to the subject matter of the following patent applications, all commonly owned herewith:

PCT Application No. US/2006/41028, filed Oct. 19, 2006, entitled "Multifunction Warming Device for Perioperative Use", and published on Apr. 26, 2007 under Publication No. WO2007/047917;

PCT Application No. PCT/US2007/013073, filed Jun. 1, 2007, titled "Warming Device", and published Jan. 31, 2008 under Publication No. WO 2008/013603;

PCT Application No. PCT/US2008/000141, filed Jan. 4, 2008, titled "Convective Warming Device with a Drape", and published Jul. 31, 2008 under Publication No. WO 2008/091486;

U.S. patent application Ser. No. 10/895,672, filed Jul. 21, 2004, entitled "Perioperative Warming Device", now abandoned, published on Jan. 20, 2005, under Publication No. US 2005/0015127;

U.S. patent application Ser. No. 11/057,397, filed Feb. 11, 2005, entitled "Thermal Blanket for Warming the Limbs", and published on Aug. 17, 2006 under Publication No. US 2006/0184216, now U.S. Pat. No. 7,520,889;

U.S. patent application Ser. No. 11/492,425, filed Jul. 25, 2006, entitled "Warming Device", and published on Nov. 16, 2006 under Publication No. US 2006/0259104;

U.S. patent application Ser. No. 11/583,432, filed Oct. 19, 2006, entitled "Multifunction Warming Device for Perioperative Use", and published on Apr. 26, 2007 under Publication No. US/2007/0093882;

U.S. patent application Ser. No. 11/583,480, filed Oct. 19, 2006, entitled "Multifunction Warming Device with Provision for Warming Hands", and published on Apr. 26, 2007 under Publication No. US/2007/0093884;

U.S. patent application Ser. No. 11/583,481, filed Oct. 19, 2006, entitled "Multifunction Warming Device with an Upper Body Convective Apparatus", and published on Apr. 26, 2007 under Publication No. US/2007/0093885;

U.S. patent application Ser. No. 11/656,777, filed Jan. 23, 2007, entitled "Convective Warming Device With a Drape";

U.S. patent application Ser. No. 11/704,547, filed Feb. 9, 2007, entitled "A Forced Air Warming Unit";

U.S. patent application Ser. No. 11/801,292, filed May 9, 2007, titled "Warming Device with Varied Permeability", and published on Oct. 11, 2007 under Publication No. US 2007/023939;

U.S. patent application Ser. No. 11/899,872, filed Sep. 7, 2007, entitled "Perioperative Warming Method"; and published on Jan. 31, 2008 under Publication No. US 2008/0027522;

U.S. patent application Ser. No. 11/899,928, filed Sep. 7, 2007, entitled "Perioperative Warming Device" and published on Jan. 31, 2008 under Publication No. US 2008/0027521;

U.S. patent application Ser. No. 12/011,699, filed Jan. 1, 2008, titled "Warming Device" and published on Jun. 11, 2009 under Publication No. US 2009/0149931;

U.S. patent application Ser. No. 12/386,243, filed Apr. 15, 2009, titled "Warming Device with Provisions for Deploying Elements of an Upper Body Convective Apparatus and for Deploying the Lower Portion of the Warming Device" and published on Sep. 10, 2009 under Publication No. US 2009/0228083; and U.S. patent application Ser. No. 12/653,825, filed Dec. 21, 2009, titled "Warming Device Constructions with a Poncho-Type Patient Gown".

BACKGROUND

The field covers a multifunction warming device including a clinical garment with an elongate convective apparatus supported on the inside of the garment, transversely to the garment, running between its sleeves.

In this specification, use of the term "convective" to denote the transfer of heat from a device to a body refers to the device's principal mode of heat transfer, it being understood that heat may at the same time be transferred from the device to the body by conduction and radiation, although not to the degree of convection.

Convective devices that transfer heat to a human body are known. For example, there are devices that receive a stream of pressurized, warmed air, inflate in response to the pressurized air, distribute the warmed air within a pneumatic structure, and emit the warmed air onto a body to accomplish such objectives as increasing comfort, reducing shivering, and treating or preventing hypothermia. These devices are typically called "convective thermal blankets" or "covers"; for convenience, in this discussion and the following specification, they shall be called, simply, "thermal blankets." Arizant Healthcare Inc., the assignee of this application, makes and sells such devices under the BAIR HUGGER® brand. One such device is the Model 522 Upper Body Blanket.

Thermal blankets have been specifically designed for particular deployments where therapeutic warming is indicated. Three representative thermal blankets known in the prior art are shown in FIGS. 1A-1D. A "full body" thermal blanket 10 is shown in FIG. 1A. The full body thermal blanket is adapted to lie upon a person and to extend longitudinally along the body of the person in order to cover substantially the person's entire body, from near the ankles or feet up to the neck. A "lower body" thermal blanket 12 is shown in FIG. 1B. The lower body thermal blanket 12 is adapted to lie upon the person and to extend longitudinally along the body of a person in order to cover the person's lower body, from near the ankles or feet up to the waist or pelvis of the person. An "upper body" thermal blanket 15 is illustrated in FIGS. 1C and 1D. The upper body thermal blanket 15 has a bow-tie shape that is adapted to lie upon and extend transversely across the upper body of a person in order to cover the person's chest and extended arms. A head drape 16 may be formed on or attached to the upper body thermal blanket 15 for draping over the head 17 of a person in order to retain warmed air expelled through the blanket 15 about the head to aid in therapeutic warming during surgery. When fed a stream of warmed pressurized air, each of the thermal blankets 10, 12, 15 inflates and distributes the air within itself. While the thermal blanket lies on the person, the warmed pressurized air flows through apertures or interstices in a permeable surface of the thermal blanket which faces the person. These thermal blankets may have one, two, or more inlet ports 18 through which an air hose 19 provides warmed pressurized air from a heater/blower unit (not shown in these drawings).

The construction of thermal blankets is well understood. Examples of specific constructions are given in U.S. Pat. No. 5,620,482, U.S. Pat. No. 5,443,488, U.S. Pat. No. 5,360,439, and U.S. Pat. No. 5,304,213. See also U.S. Pat. No. 5,974,605.

Clinical garments such as hospital gowns are widely used when patients remove clothes in preparation for surgery. A hospital gown provides a disrobed patient with privacy and dignity before and after surgery, and often remains on the patient throughout the surgical cycle. The utility of clinical garments has been expanded by a recent invention disclosed in the referenced Publication No. WO 2003/086500. The invention described in the publication adapts a clinical garment such as a robe or gown to receive a convective device such as a thermal blanket in order to warm a person wearing the garment in a clinical setting for comfort and mobility of the person. An invention covering a multifunction warming device for perioperative use is described in the referenced Publication US 2006/0122671 wherein a warming device is constituted of a clinical garment and a convective apparatus adapted for comfort and therapeutic warming that is supported on the inside surface of the garment.

The term "perioperative" is defined in the PDR Medical Dictionary, Second Edition, (Medical Economics Company, 2000), as "around the time of operation." The perioperative period is characterized by a sequence including the time preceding an operation when a patient is being prepared for surgery ("the preoperative period"), followed by the time spent in surgery ("the intraoperative period"), and by the time following an operation when the patient is closely monitored for complications while recovering from the effects of anesthesia ("the postoperative period").

According to Mahoney et al. (Maintaining intraoperative normothermia: A meta-analysis of outcomes with costs. AANA Journal. 4/99; 67, 2:155-164.), therapeutic warming is employed during at least the intraoperative period in order to prevent or mitigate effects that result from hypothermia. In fact, it is increasingly manifest that maintenance of normothermia perioperatively enhances the prospects for a quick, successful recovery from surgery. For example, maintenance of perioperative normothermia appears to be a factor in decreasing the incidence of surgical wound infections in patients undergoing colorectal surgery, (Kurz A, Sessler D I, Lenhardt R. Perioperative normothermia to reduce the incidence of surgical-wound infection and shorten hospitalization. Study of Wound Infection and Temperature Group. N Engl J. Med. May 9, 1996; 334(19):1209-1215). Other studies suggest that maintenance of perioperative normothermia improves surgical outcomes at low cost, (Harper C M, McNicholas T, Gowrie-Mohan S. Maintaining perioperative normothermia. BMJ. Apr. 5, 2003; 326(7392):721-722). The effectiveness of therapeutic warming depends upon delivery of enough heat to a patient's body to raise the patient's core body temperature to, or maintain it within, a narrow range, typically around 37° C. This range is called "normothermic" and a body with a core temperature in this range is at "normothermia." Hypothermia occurs when the core body temperature falls below 36° C.; mild hypothermia occurs when core body temperature is in the range of 34° C. to 36° C. Therefore, "perioperative therapeutic warming" is warming therapy capable of being delivered during one or more of the perioperative periods for the prevention or treatment of hypothermia.

Therapeutic warming is contrasted with "comfort warming" which is intended to maintain or enhance a patient's sense of "thermal comfort". Of course, therapeutic warming may also comfort a patient by alleviating shivering or a feeling of being cold, but this is a secondary or ancillary effect; and, comfort warming may have some therapeutic effect. However, even though thermal comfort is a subjective notion, environmental conditions that produce a sense of thermal comfort in a population of human beings are known and well tabulated. For example, Fanger (Thermal Comfort: Analysis and Applications of Environmental Engineering, Danish Technical press, Copenhagen, 1970) defines thermal comfort as "that condition of mind which expresses satisfaction with the thermal environment." Even when a patient is normothermic, less than ideal environmental conditions can result in acute feelings of discomfort. Under normothermic conditions, thermal comfort is largely determined with reference to skin temperature, not core body temperature. Comfort warming is warming applied to a patient to alleviate the patient's sense of thermal discomfort.

Therapeutic warming may be indicated during any one or more of the perioperative periods. For example, for a short operation in a surgery with no warming equipment available, a person may be warmed preoperatively in a preparation area to raise mean body temperature to a level higher than normal in order to store enough thermal energy to maintain normothermia, without heating, intraoperatively. After surgery, it may be necessary to apply therapeutic warming in a recovery area to raise the core temperature to normothermia and maintain it there for a period of time while anesthesia wears off. Alternatively, for a long surgery in an arena with heating equipment available, a person may be warmed for comfort before surgery and warmed therapeutically during and after surgery.

Therapeutic warming is typically provided by convective devices such as the thermal blankets shown in FIGS. 1A-1D. An example of use of a full body thermal blanket for therapeutic warming is found in U.S. Pat. No. 6,524,332, "System and Method for Warming a Person to Prevent or Treat Hypothermia", commonly owned with this application.

The upper body thermal blanket 15 shown in FIGS. 1C and 1D is frequently used during thoracic, abdominal and pelvic surgery and/or in the post anesthesia care unit (PACU) to satisfy the need for therapeutic warming. As is known, a patient's core body temperature can drop to hypothermic levels quickly during surgery. To prevent or mitigate the effects of hypothermia, an upper body blanket may be deployed for therapeutic warming during the intraoperative period. However, the need for therapeutic warming often is ascertained only after surgery commences and it is inconvenient, and sometimes it is not possible, to interrupt attendance on a patient during a surgical procedure in order to locate and deploy a thermal blanket and bring it into operation. In such cases, therapeutic warming can be delayed until the patient enters the PACU, when the patient may have been hypothermic for a significant period of time. Given the frequency with which upper body thermal blankets are used during and after surgery, it would be very useful and clinically beneficial to conveniently position an upper body convective device with respect to a patient so that it could be quickly accessed and deployed during thoracic, abdominal, or pelvic surgery with little or no time spent in retrieval.

A warming device combining a clinical garment with a convective insert to provide comfort warming does not provide for therapeutic warming during thoracic surgery. Thus, even for a patient wearing a clinical garment with a convective apparatus as disclosed in WO 2003/086500, an upper body thermal blanket must be unpackaged, made ready and deployed during such surgery. Warming may be indicated postoperatively in order to stave off hypothermia while the patient's recuperation proceeds. Manifestly, a substantial convenience and a significant gain in a patient's physical condition would result from use of a warming device capable of clothing a patient preoperatively, while positioning a convective apparatus to therapeutically warm the patient during thoracic, abdominal, or pelvic surgery and postoperatively. Because of wide-spread and frequent use, it would be particularly desirable to have a multifunction warming device constituted of a clinical garment with a convective apparatus supported on the inside of the garment for easy deployment and use in warming a patient's upper body.

The assignee's Publication US 2006/0184217 published Aug. 17, 2006 discloses a warming device for perioperative use in which thermal blankets are attached to the inside surface of a clinical garment. However, use of the thermal blankets for therapeutically warming a patient wearing the clinical garment requires either that the thermal blanket be detached from the inside surface and repositioned for use, or that the clinical garment be removed from the patient and repositioned in order to correctly orient the thermal blanket with respect to the patient. In either case, the extra steps to access the thermal blanket for operation complicate use of the warming device, and consume time otherwise spent tending to the patient.

The deterrents to adoption of the warming device disclosed in US 2006/0184217 are eliminated by disposing an elongate convective thermal blanket for upper body use on the inside of the clinical garment, transversely to the garment, between its sleeves, with its permeable surface facing the patient. This positioning of the convective apparatus in the clinical garment locates it against the chest of a patient wearing the garment and permits it to be deployed and used on the patient during and after surgery without removal of the clinical garment from the patient, without removal of the convective apparatus from the gown, and without reorientation of the clinical garment in order to correctly orient the convective apparatus with respect to the patient.

SUMMARY

A multifunction warming device includes a clinical garment having an inside surface supporting a convective apparatus disposed to provide therapeutic warming of a patient's upper body during surgery. The warming device includes a clinical garment with an elongate convective apparatus supported on the inside of the garment, transversely to the garment, and running between its sleeves. The positioning of the convective apparatus in the clinical garment locates it against the chest of a patient wearing the garment and permits it to be deployed and used on the patient's upper body during and after surgery without removal of the clinical garment from the patient or removal of the convective apparatus from the gown.

BRIEF DESCRIPTION OF THE DRAWINGS

FIGS. 3B and 3C are plan views of the convective apparatus used in the multifunction warming device. FIG. 3C shows details of folding elements of the convective apparatus.

FIG. 3D is a plan view of the convective apparatus of FIGS. 3B and 3C with portions of its sleeves folded.

FIG. 3E is an enlarged, partially schematic drawing showing an operation of an attachment mechanism.

SPECIFICATION

A multifunction warming device for perioperative use is constituted of a clinical garment and at least one convective apparatus supported on an inside surface of the garment. In this regard, a "clinical garment" is a garment that is typically used to temporarily clothe a patient in a clinical setting. Such garments include hospital gowns, robes, bibs and other equivalents. The clinical setting may be a medical or dental office or clinic, a hospital, or any facility or institution that provides medical or dental treatment to patients. A convective apparatus receives and distributes at least one stream of warmed pressurized air in a structure for being disposed on, adjacent, or next to the core and/or the limbs of a body. When pressurized with warmed air, a convective apparatus emits warmed air through one or more permeable surfaces.

In one aspect, a multifunction warming device for perioperative use may be worn on a person where it receives a stream of warmed pressurized air, distributes the pressurized air within a convective apparatus, and emits the air through one or more surfaces of the convective apparatus to warm the person's body.

In another aspect, the multifunction warming device may be adapted for therapeutic warming during surgery. In this regard, the multifunction warming device may be adapted for therapeutic warming by deploying a convective apparatus for use intraoperatively while the clinical garment is furled so as not to intrude on the surgical site.

In the warming device illustrated and discussed below, convective apparatuses are inflatable. That is, their structures, flaccid when not in use, tauten when receiving a stream of pressurized air.

Although a single convective apparatus is set forth in the following description and shown in the illustrations, this is not meant to exclude the provision of one or more additional convective apparatuses provided on the inside surface of the clinical garment for comfort or therapeutic warming. Thus, reference will be made in the specification and the claims which follow to "one or more" convective apparatuses.

Figure 1A:
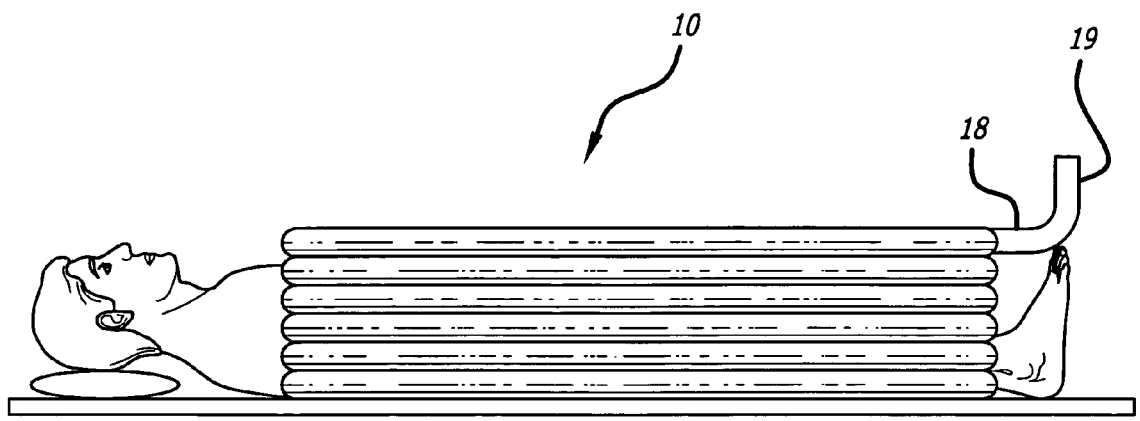
FIGS. 1A-1D are illustrations of prior art full body, lower body, and upper body convective thermal blankets.
Figure 1B:
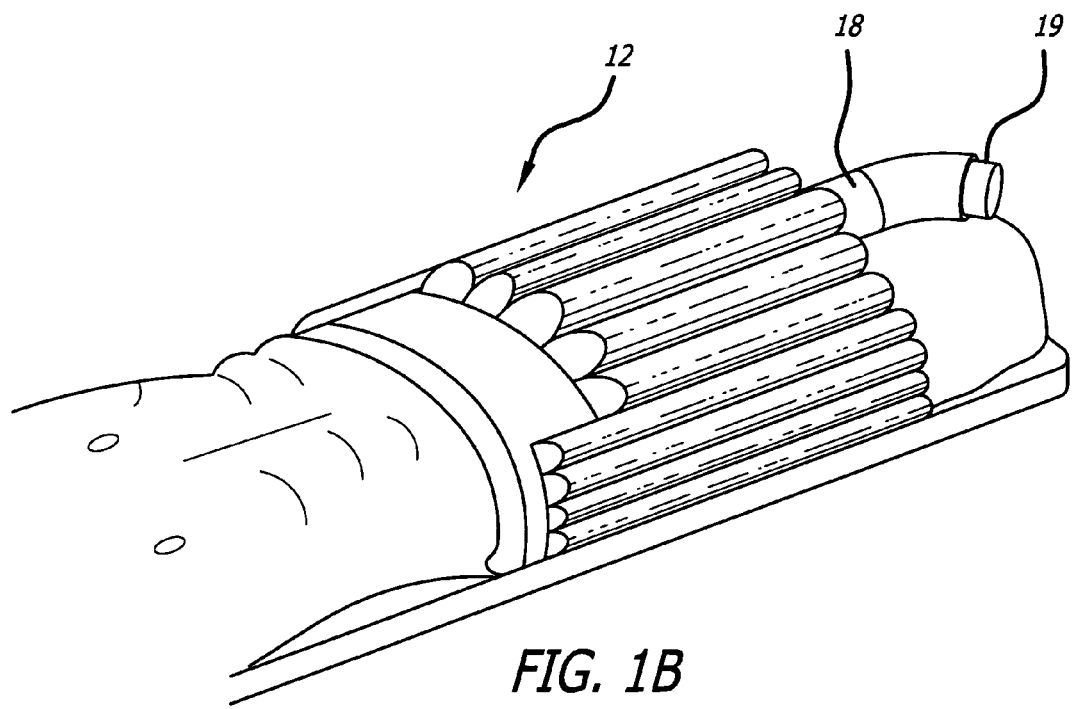
Figure 1C:
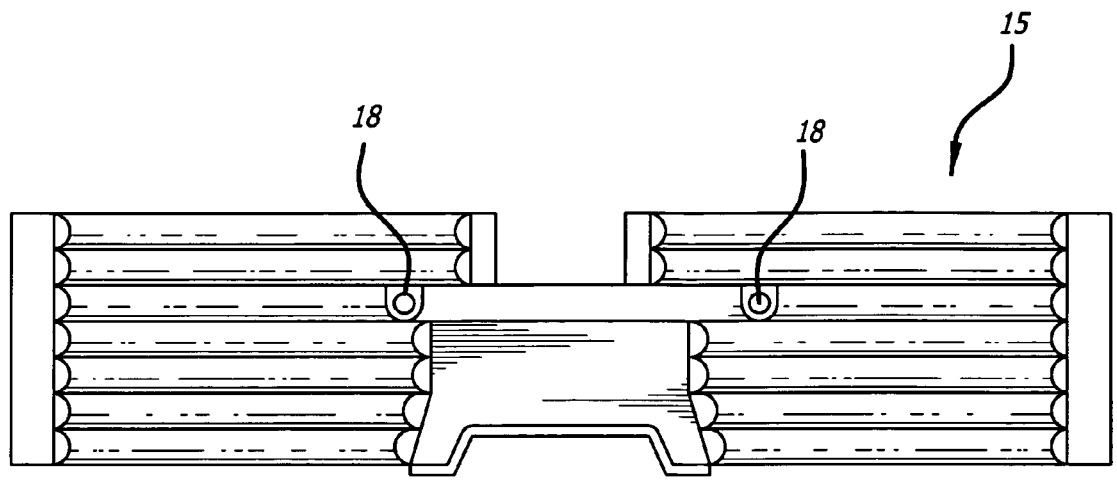
Figure 1D:
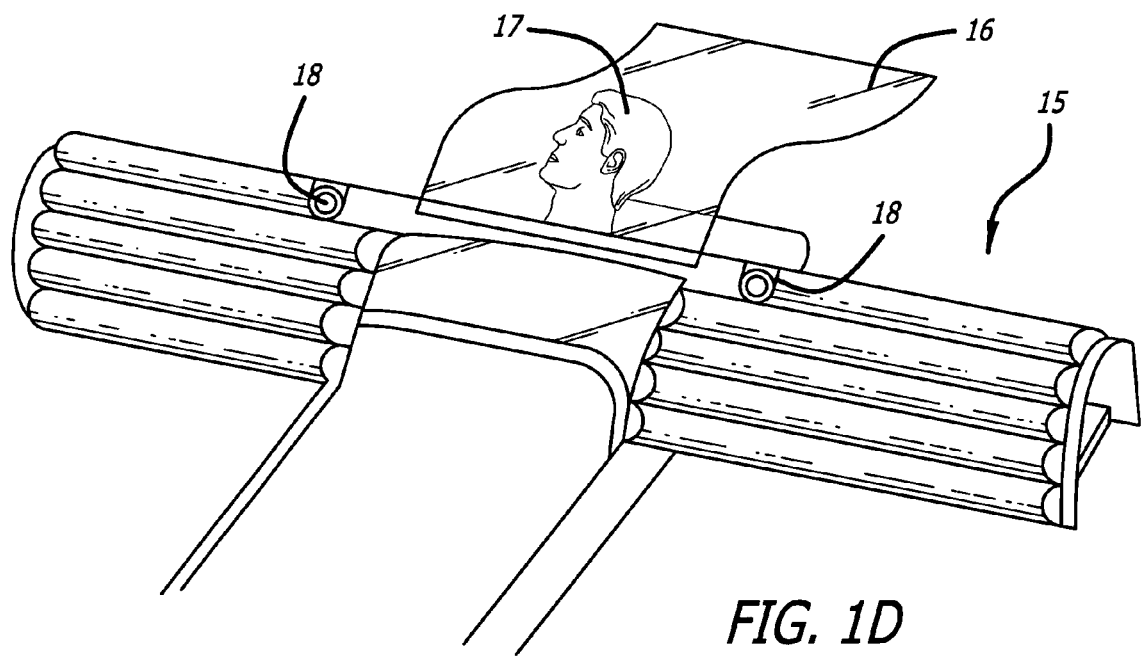
Figure 2:
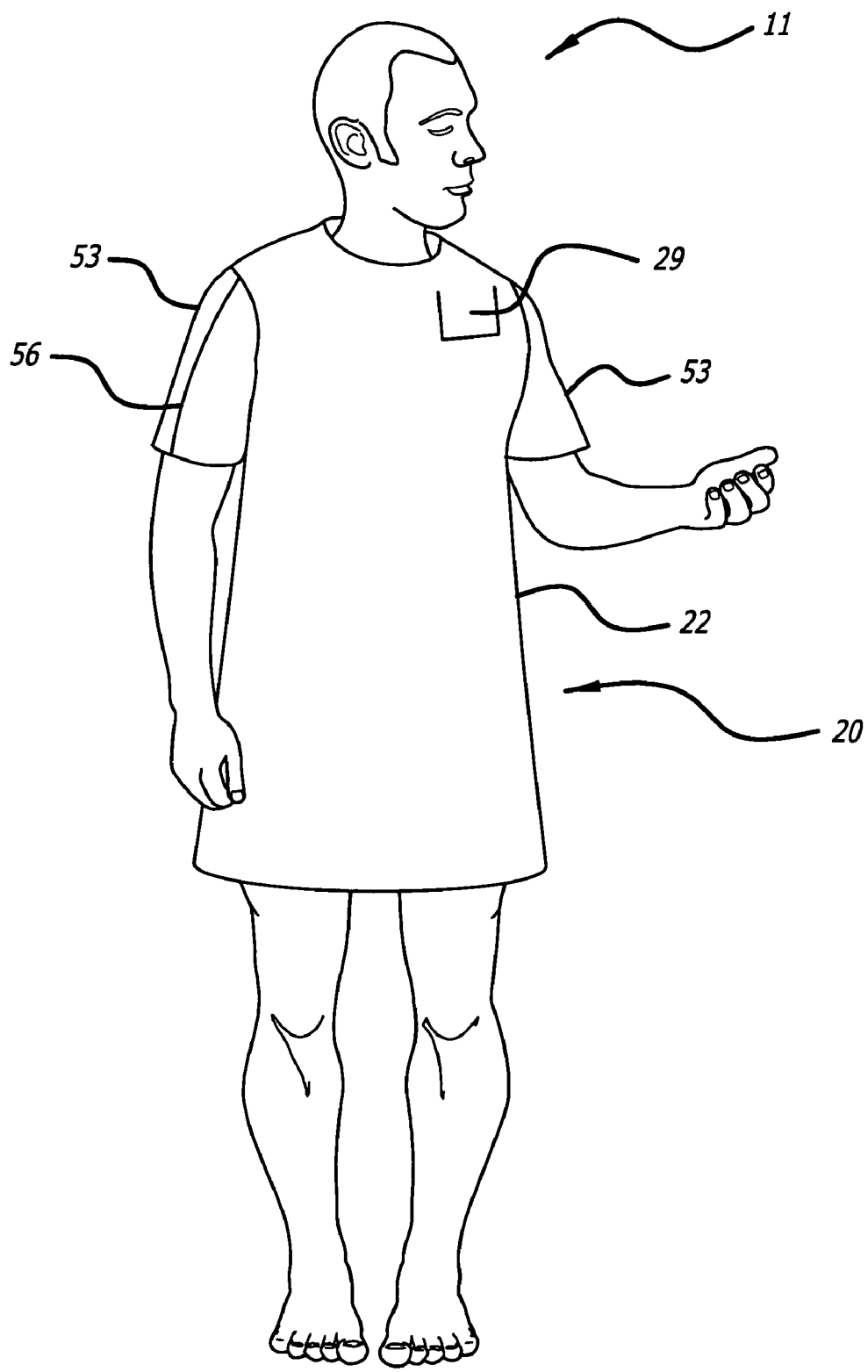
FIG. 2 is an illustration of a person wearing a multifunction warming device.

Refer now to the figures, in which a person 11 wearing a multifunction warming device 20 for perioperative use is illustrated in FIG. 2. The warming device 20 is constituted of a clinical garment 22 and at least one convective apparatus (not seen in this view) supported on an inside surface of the clinical garment 22. The convective apparatus may be operated by receiving warmed, pressurized air from a heater/blower unit (not seen in this view) through an air hose with a nozzle that is received in an inlet port of the convective apparatus. The inlet port is accessed through a flap 29 in the clinical garment 22. Other inlet ports (not shown) may be accessed through other flaps in the clinical garment (not shown).

Figure 3A:
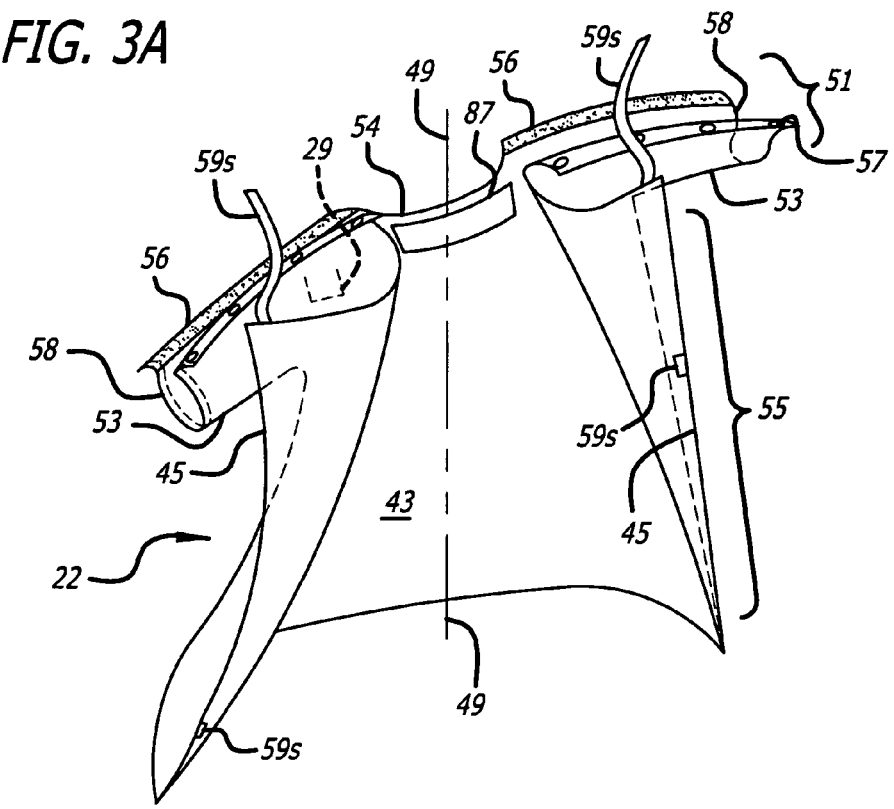
FIG. 3A is a perspective view from behind a clinical garment, with the clinical garment partially opened to show an inside surface that supports two convective warming apparatuses.
Figure 3F:
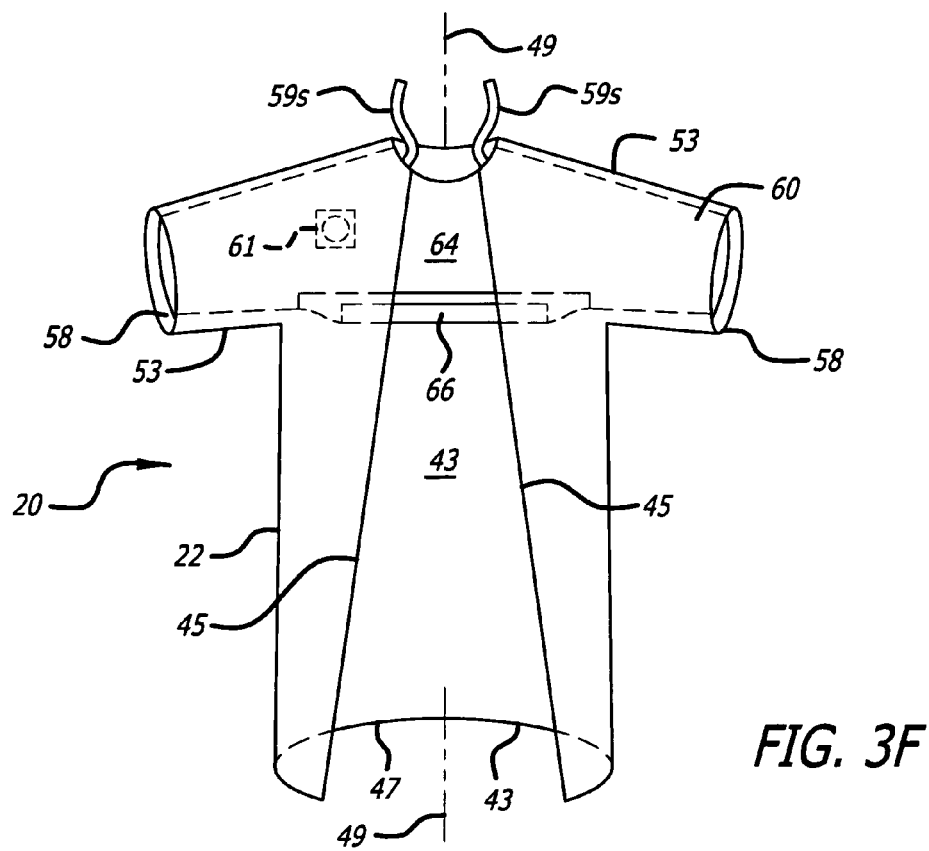
FIG. 3F is a rear elevation view of a multifunction warming device for perioperative use.

FIGS. 3A-3D illustrate the elements of a multifunction warming device for perioperative use; the assembled multifunction warming device 20 is itself illustrated in FIG. 3E. The view in FIGS. 3A and 3F is from the rear of the clinical garment 22, looking toward the inside surface of the garment, which faces the chest, or thorax of a patient and on which at least one convective apparatus is mounted. FIGS. 3B through 3D are plan views of an uninflated convective apparatus, looking toward a permeable surface through which air is expelled toward a patient when the blanket is inflated. As seen in FIGS. 3A and 3F, the warming device 20 includes the clinical garment 22. The clinical garment 22 includes an inside surface 43, two opposing lateral hems 45, a lower hem 47, and a longitudinal axis 49. The clinical garment 22 has an upper portion 51 with two opposing sleeves 53 (also seen in FIG. 2) and a scooped upper edge 54, and a lower portion 55. The flap 28 that provides access to an inlet port through the front of the garment 22 is also visible in FIG. 3A. The sleeves 53 may be long or short. Short sleeves are preferred if access must be had to a person's arms for instrumentation and/or IV delivery. Each sleeve 53 includes an elongate seam 56 (both seen closed in FIG. 2). Each seam 56 may be held closed by means 57 including, for example, buttons, snaps, hook and loop material, tape, and/or straps, or any equivalent thereof. Such means can be operated to let a seam 56 be opened and to again close a seam, once opened. Cuffs 58 may be formed in the clinical garment 22 inside the sleeves 53, near the ends of the sleeves 53. The clinical garment 22 may open on a side. Preferably, the clinical garment 22 opens in the rear. The opening may be full, as illustrated in FIG. 3A, or it may be a slit rising from the lower hem 47. As per the example shown in FIG. 3A, the opening may be closed by means 59s along the lateral hems 45 which releasably connect to keep the hems together. Such means may include, for example, buttons, snaps, hook and loop material, tape, and/or straps, or any equivalent thereof. In keeping with the example of FIG. 3A, if straps are used to close the opening, the straps may be attached to the clinical garment 22, or formed integrally therewith as a step in manufacturing the clinical garment 22. For example only, two integrally-formed straps 59s for tying the opposing lateral hems 45 together in the upper portion 51 are seen in FIG. 3A. Two additional straps may be attached to the outside surface of the clinical garment 22 with enough reach to be tied together around the outside of the clinical garment, near its middle. With enough overlap of the lateral hems 45, the opening in the clinical garment 22 can be completely closed and secured, with the lateral hems overlapping to afford concealment of a patient's private parts. The clinical garment 22 may be constructed from non-woven or woven materials. Preferably, the clinical garment 22 is made from a non-woven blend of spunlace polyester and wood pulp In FIG. 3B, an elongate convective apparatus 60 is shown fully opened for deployment to provide therapeutic warming. In FIG. 3C, elements of the convective apparatus 60 are shown folded. The view in both figures is toward a permeable surface of the convective apparatus 60 through which heated air is expelled when the blanket is inflated. As seen in these figures, the convective apparatus 60 includes an inlet port 61, two laterally-extending arms 62, each transitioning to a respective end 63, a permeable surface 64, and a lower edge 65. Each end 63 has a generally quadrilateral configuration with a periphery 63p. Typically, the periphery 63p includes a seal with some width. In some aspects of the convective apparatus 60, ties 63t may be integrally formed or defined in the peripheries 63p by lines of weakness or perforations 63w. One tie 63t is shown in dashed outline in FIG. 3B separated from the periphery 63p in which it is formed. Such ties may be used when the convective apparatus 60 is deployed for use in securing the convective apparatus 60. As can be appreciated, from the separated tie 63t, the arcuate shape near the end of the tie provides easy handling for tying to another tie, to a patient, or to equipment in the surgical area. See the assignee's U.S. Pat. No. 5,773,275 in this regard. Optionally, slits 63s may be formed in seals near the outer edges of the ends 63. The slits 63s may be defined in the seals by lines of perforations. If provided, the slits 63s may be opened to be used as purchase holds for unfurling the ends 63 and/or for receiving the hands on the outstretched arms of a patient in order to anchor or secure the ends 63 such as when the convective apparatus 60 is inflated and operated.

For stowing the convective apparatus 60 prior to use, the opposing sides of the ends 63 may be folded toward each other as indicated by the arrows 68a in FIG. 3B, and then folded as indicated by the arrow 68b in FIG. 3C. The folds 68 reduce each end 63 to a length that fits in a respective sleeve 53 of the clinical garment 22. The folds are preferably made so as to be easily tucked between the clinical garment 22 and the convective apparatus 60. The ends of the folded configurations may be retained in the inside cuffs 58 in the sleeves of the clinical garment 22. This allows the patient to insert an arm through the sleeve of the clinical garment 22 without catching the corresponding hand on the fold and inadvertently deploying the extended side. Preferably, the ends 63 are folded by a Z-fold, although a gatefold, accordion fold or any equivalent fold may be used. More generally, the ends 63 may be folded, rolled or gathered in any way that achieves the desired length reduction and neat compaction useful for stowing and retaining the ends 63 in the cuffs 58, and unfolding them when the convective apparatus is to be used for therapeutic warming. The convective apparatus 60 has a line of weakness or perforation that extends transversely at 69 between each end 63 and a respective laterally-extending side 62.

With further reference to FIGS. 3B and 3C, in some aspects the convective apparatus 60 may include an attachment mechanism, preferably in the form of double-sided tape 66. Preferably, the double-sided tape 66 is attached on one side of the convective apparatus 60 to a sealed lower portion of the permeable surface 64 of the convective apparatus 60, along the lower edge 65, centered between the ends 63. Referring to FIG. 3B, the surface 66b of the double-sided tape 66 that is visible is covered with a non-adhesive backing that can be stripped off to expose the adhesive with which both sides of the tape are covered. For convenience, the sealed lower portion of the permeable surface 64 where, the attachment mechanism is mounted may be surrounded by a perforation 66p which allows either side of the attachment mechanism to be detached from the sealed lower portion and permit the attachment mechanism to pivot on its longitudinal edge. The perforation 66p also permits the attachment mechanism to be removed after use.

With reference to FIGS. 3B and 3C, although one inlet port 61 is illustrated in the convective apparatus 60, one or more additional inlet ports may be provided for convenience. Unused inlet ports are sealed or closed by known means to prevent air escaping therethrough. Preferably the inlet port 61 is provided through the surface of the convective apparatus 60 which is not visible in this figure; it may also be provided through an edge of the convective apparatus 60. The inlet port 61 may comprise a collar 61a of stiff material with an opening 61b to receive the nozzle of an air hose, or it may comprise a sleeve of material, or any other equivalent structure. When the convective apparatus 60 is used for therapeutic warming, the ends of the sleeves are removed from the cuffs 58 and unfolded. Then, warmed pressurized air flowing through an inlet port such as the inlet port 61 inflates the convective apparatus 60, from its central portion to its ends 63.

An operation for deploying the double-sided tape for use is shown in FIG. 3E. The double-sided tape 66 is adhered, on one side, to the convective apparatus 60 centered along the lower edge 65. Backing 66b is mounted to the surface of the tape 66 that faces a patient wearing the warming device 20. When the tape 66 is deployed for use, the two short sections of the perforation 66p (best seen in FIGS. 3B and 3C) may be torn. This permits the portion of the convective apparatus 60 to which the double-sided tape 66 is attached to pivot on its longitudinal edge so that the lower edge 65 with the double-sided tape 66 mounted therealong may be swung toward and away from the patient. The backing 66b may be stripped off and the tape 66 may be adhesively attached to the skin of the patient, thereby anchoring the warming device 20 and/or the convective apparatus 60. As explained hereinabove with reference to FIGS. 3B and 3C, the double-sided tape 66 may be removed after use by tearing along the long section of the perforation 66p. Alternatively, the tape 66 may be rotated behind the lower edge 65, between the convective device 60 and the inside surface 43, once the tape has been released from the patient.

A head drape 87, shown unfurled in FIG. 3E and furled or folded in FIGS. 3A-3D, preferably constituted of a sheet of clear plastic, may be attached to the inside surface 43 of the clinical garment 22, near the scooped upper edge 54 (shown in FIG. 3A) or may be attached near the upper edge of the convective apparatus 60 on the surface which faces the inside surface 43 (shown in FIGS. 3B through 3D).

FIG. 3F shows a multifunction warming device 20 for perioperative use assembled from the elements illustrated in FIGS. 3A-3E. As illustrated in FIG. 3F, the convective apparatus 60 is an elongate convective apparatus disposed, supported, or constructed on the inside surface 43 of the clinical garment 22, in the upper portion 51, transverse to the longitudinal axis 49 and extending from sleeve 53 to sleeve 53. Preferably, the convective apparatus 60 is an upper body convective apparatus having the construction illustrated in FIGS. 3B and 3C, with its ends 63 folded and retained in the inside cuffs 58. An opening in the upper portion 51 of the clinical garment 22 (such as the flap 29 in FIGS. 2 and 3A) provides access by which an air hose can connect to one or more inlet ports such as the inlet port 61 of the convective apparatus 60 in order to operate the blanket for therapeutic warming. In use, warmed, pressurized air flows into and inflates the convective apparatus 60, and exits through the permeable surface 64 toward a patient.

The convective apparatus 60 may be formed by joining two sheets of material with a closed impermeable seam around their peripheries. One of the sheets is relatively impermeable and the other sheet is relatively more permeable to permit airflow therethrough. The sheets are further connected by discontinuous seals or stake points within the closed impermeable seams. The two sheets with which a convective apparatus is formed may be separate from the clinical garment 22, in which case the convective apparatus is permanently or releasably attached, fixed, or adhered to the inside surface 43 of the clinical garment 22, with its permeable surface facing inwardly, toward a patient wearing the device 20. An exemplary construction in this regard is illustrated in FIGS. 1A and 1D and FIGS. 3A-3C of PCT publication WO 2003/086500. Alternately, the convective apparatus 60 may be formed or constructed integrally with a clinical garment 22 made of relatively impermeable material by attaching a relatively permeable sheet to a portion of the inside surface of the clinical garment 22. An exemplary construction in this regard is illustrated in FIGS. 1D and 1E and FIGS. 3D-3F of PCT publication WO 2003/086500.

According to the present best mode of construction of the multifunction warming device for perioperative use, the convective apparatus is formed or assembled separately from the clinical garment and then attached to its inside surface by sewing, gluing, heat sealing, or welding, or any combination of these. The convective apparatus 60 is formed by heat sealing two sheets of material together. The sheets include a laminate sheet comprising a layer of nonwoven material on which a layer of polypropylene is extruded, and a polypropylene film. Apertures are formed through the laminate sheet to render it permeable and the polypropylene layers are sealed around their peripheries to form the convective apparatus 60. The side of the convective apparatus 60 with the relatively non-permeable polypropylene film is attached to the inside surface of the clinical garment and the nonwoven material of the laminate sheet faces the patient. The reason for locating the polypropylene film on the inside surface of the clinical garment is to reduce the bulk and stiffness of the convective apparatus, thus making the warming device more comfortable to the patient.

When the multifunction warming device 20 is worn as shown in FIG. 2 for comfort warming, a convective apparatus may be connected to a heater/bower unit via an air hose to receive a stream of warmed pressurized air. The convective apparatus inflates in response to the stream of air and emits air through its permeable surface. The multifunction warming device 20 retains warmed air within the clinical garment 22 for comfort warming.

Figure 4A:
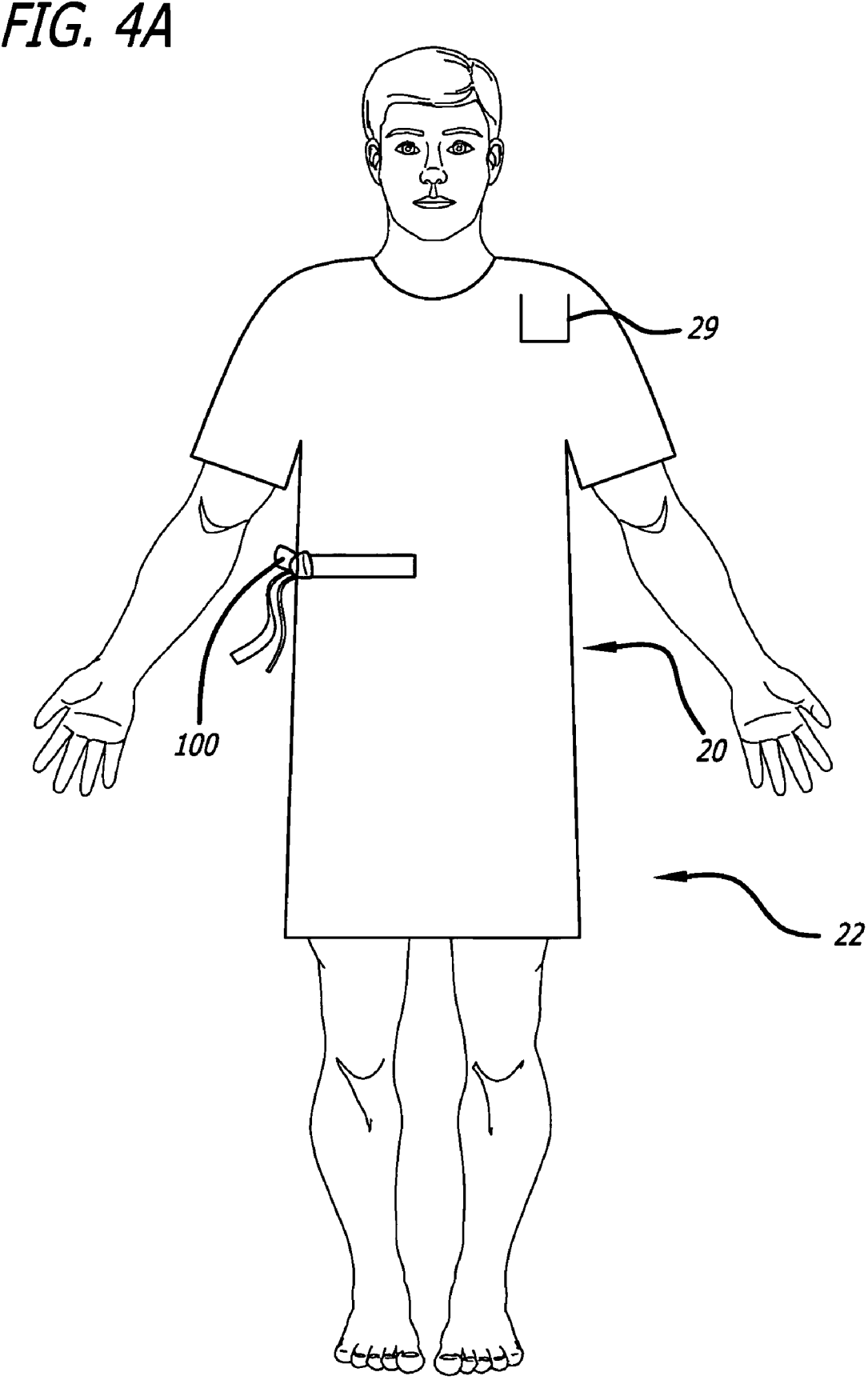
FIGS. 4A-4C illustrate preparation and deployment of a multifunction warming device for perioperative use to therapeutically warm a patient.
Figure 4B:
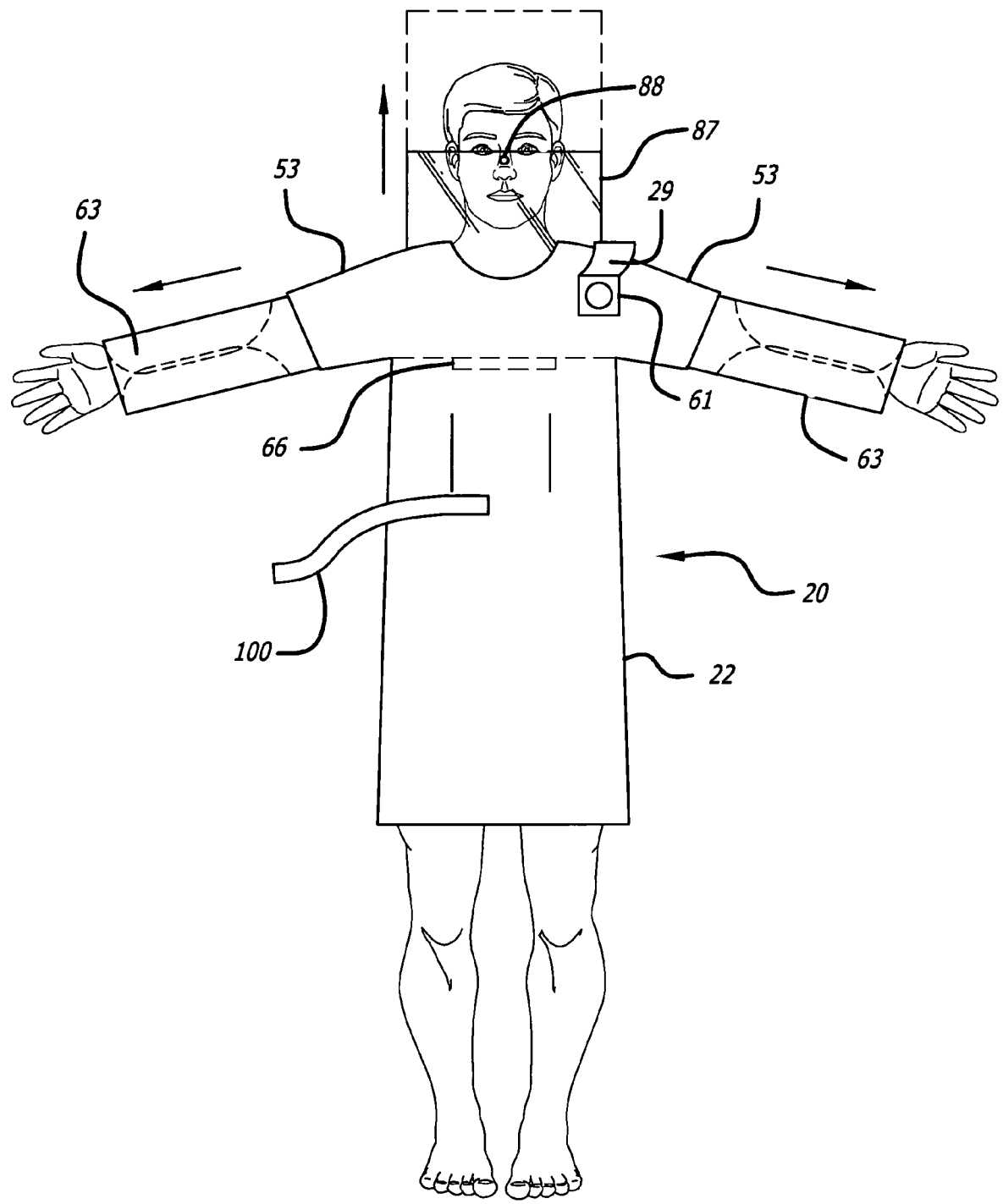
Figure 4C:
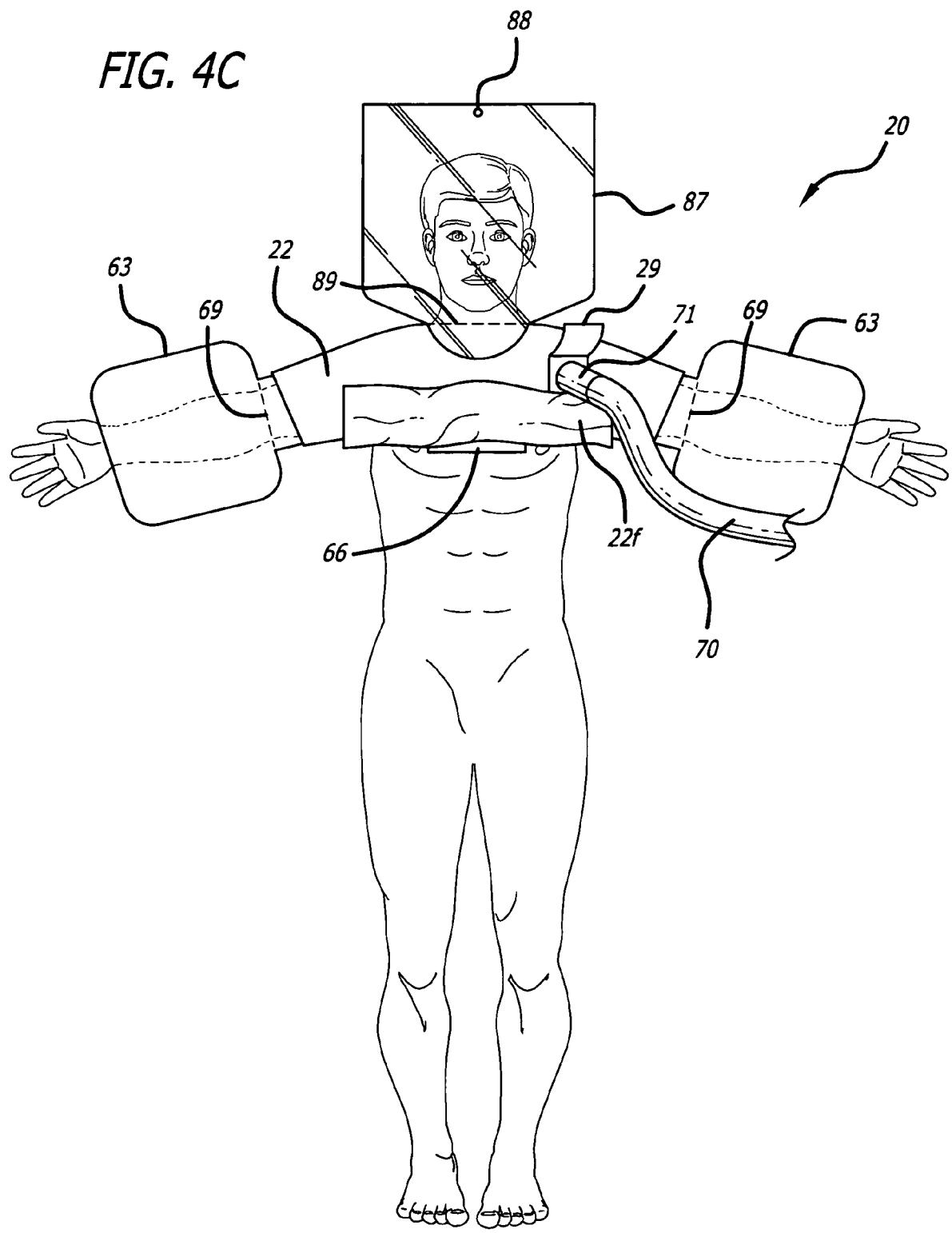

FIGS. 4A-4C illustrate how the multifunction warming device 20 is adapted for therapeutic warming by using the convective apparatus 60 in the same manner as an upper body thermal blanket. The view in these figures is toward the front of the clinical garment 22, from a position above the patient, who is lying prone on an operating table (not shown), preferably one with cruciate support for the patient's arms. In FIG. 4A, a patient is shown wearing a warming device 20 as preparation commences Ties 100 hold the clinical gown 22 closed. In FIG. 4B, the ties 100 are untied, and the head drape 87 is unfurled, as are the ends 63 of the convective apparatus 60. A grasping target 88 (also seen in FIGS. 3B-3D), or a tab, not shown, may be provided on a free upper edge of the head drape 87 so that the drape may be grasped for deployment. The ends 63 are freed from the cuffs 58, unfurled through the ends of the sleeves 53 and unfolded to be positioned over the hands and wrists of the patient.

In FIG. 4C, the flap 29 has been folded back to expose the inlet port 61 of the convective apparatus 60 and a heater/blower unit (not shown) may now be connected to the inlet port 61 via an air hose 70 and nozzle 71. As explained above in connection with FIG. 3E the double-sided tape 66 is deployed for use. That is to say, the backing 66b is pulled off the tape's outer surface. As seen in FIG. 4C, the ends 63 of the convective apparatus 60 and head drape 87 are fully unfurled, the tape 66 is adhesively attached to the patient's body, and the lower portion of the clinical garment 22 is furled or folded at 22f, thereby removing the lower portion of the multifunction warming device 20 from the surgical site. FIG. 4C shows the convective apparatus 60, in the form of an upper body convective device, deployed over and secured to the patient, and operated thereat to provide therapeutic warming during thoracic, abdominal, or pelvic surgery. In operation, the convective apparatus 60 is connected to an air hose 70, through a nozzle 71 received in the inlet port 61. The air hose is connected to a heater/blower unit (not shown) and inflates in response to a stream of air conducted through 70, 71, and 61 from the heater/blower unit and emits warmed air through its permeable surface toward the patient. The head drape 87 and unfurled ends 63 trap warm air around the patient's head and hands, which contributes to maintaining the core temperature at or near normothermia.

Figure 5A:
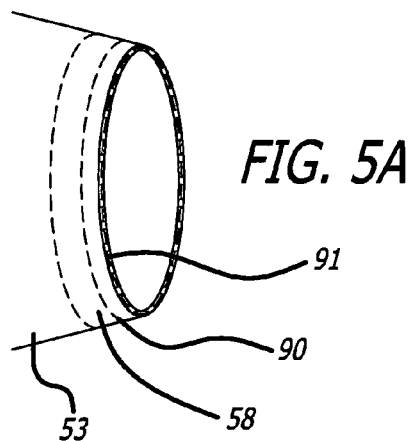
FIGS. 5A-5E are views of the front of the left sleeve of the clinical garment, looking toward the front surface of the clinical garment, showing lines of weakness that may be operated to provide access to ends of the first convective apparatus.
Figure 5B:
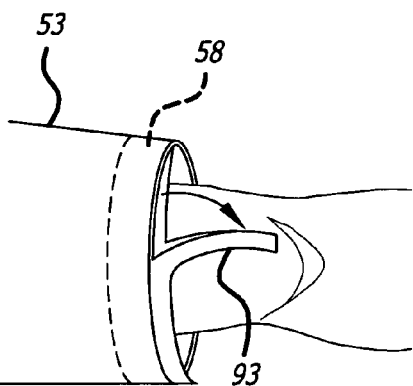
Figure 5C:
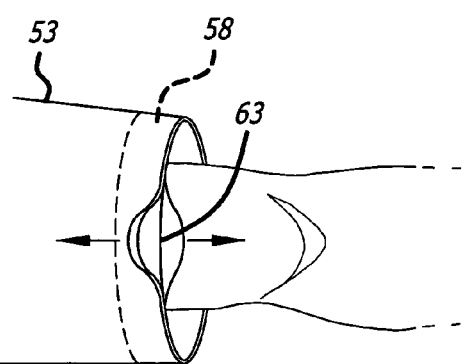
Figure 5D:
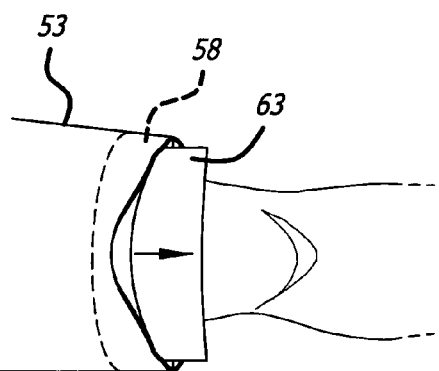
Figure 5E:
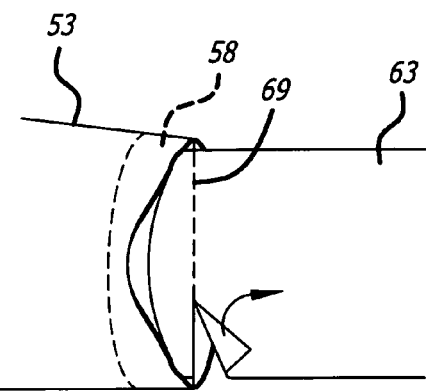

With reference to FIG. 4C, after surgery, when the heater/blower unit is disconnected from the convective apparatus 60, the ends 63 may be removed along the perforations 69 seen in FIGS. 3B, 4C, and 5E, or the convective apparatus 60 may left intact to continue being used for warming in the postoperative period. The upper portion of the head drape 87 may be detached along the line of perforations 89 seen in FIG. 4C, or the head drape may be left intact to continue being used for warming in the postoperative period. With reference to FIG. 4C, the furled portion 22f of the clinical garment 22 may be unfurled or unfolded from the center of the convective apparatus 60 toward the patient's feet thereby reconfiguring the clinical gown 22 to be worn again by the patient. Alternatively, if the patient is to be warmed postoperatively while recovering from anesthesia, the unfurled clinical gown 22 can serve as a blanket or drape over the patient to trap warm air about the patient.

The best current mode and preferred embodiment for unfurling the folded ends 63 of the convective apparatus through the ends of the sleeves 53 may be understood with reference to FIGS. 5A-5E, in which the view is toward the front surface of the left sleeve of the clinical garment 22. Thus, although it uses the left sleeve for illustration, the following explanation also applies to a corresponding construction of the right sleeve. FIG. 5A shows lines of weakness (preferably, perforations) formed in the sleeve 53 to enable access to an end 63 folded and tucked into a cuff 58. Two opposing lines of perforations 90 may be formed near the end of the sleeve 53, one in the front half of the sleeve, and an opposing one in the half of the cuff 58 that faces the front half of the sleeve. Alternately, a single line of perforations 91 may be formed at or near the end of the sleeve, where the sleeve transitions into the cuff 58. As best seen in FIG. 5B, the first pattern of perforations 90 enables a user to tear away the end 93 of the front half of the sleeve 53. The second pattern of perforations 91 permits a user to separate the two sides of the end of a sleeve, at or near the end of the sleeve 53 in the manner illustrated in FIG. 5C. As seen in FIG. 5D, once the end of a sleeve 53 is opened, the folded portion of the end 63 of the convective apparatus 60 can be pulled through the now-opened end of the cuff 58, through the end of the sleeve 53.

The best current mode for forming the cuffs 58 inside the sleeves 53 with respect to lines of perforation 90 or 91 may be understood with reference to FIGS. 3A, 3D, 3F, and 5A-5C. In this regard, the preferred pattern of perforations is formed in the front halves of the sleeves 53 of the clinical garment 22. The convective apparatus 60 is formed separately from the clinical garment 22 as described above. The convective device 60 is brought against the inside surface 43 in the fully folded configuration shown in FIG. 3D, running between the sleeves 53, with its impermeable surface facing the inside surface 43 and the folded configurations of the ends 63 located therebetween. The convective apparatus 60 is attached to the inside surface 43 by lines of adhesive bonding between its upper and lower edges and the portion of the inside surface in the front halves of the sleeves 53. Toward the ends of the sleeves, the lines of adhesive bonding stop short of the folded portions of the ends 63 and the perforations 90; in the direction of the longitudinal axis 49, the lines of bonding stop where the sleeves 53 join the main body of the clinical garment 22. A line of adhesive stake points between the impermeable surface of the convective apparatus 60 and the inside surface is provided just above the attachment mechanism 66. The end of each sleeve 53 is then folded inwardly of the sleeve 52, toward and along the inside surface 43, far enough to position the two lines of perforations 90 opposite each other, one line inside and the other line outside of the sleeve, or to position the single line of perforations 91 at or near the transition to the inside cuff 58. Once folded, the end of each sleeve is attached inside the sleeve by a single elongate strip of adhesive bonding extending transversely across the sleeve. With reference to FIGS. 3A and 3D, the strip of bonding for each cuff 58 may be as wide as the cuff. As may be further appreciated with reference to these figures, the strip of adhesive bonding along a cuff 58 runs between the cuff and a trace extending from a portion of the inside surface 43 in the sleeve 53 above the upper edge 62 of the convective apparatus 60, across a narrow strip of the permeable surface 64 of the convective apparatus 60 in the front half of the sleeve, and across a narrow strip of the inside surface in the back half of the sleeve. When the perforation pattern near or at the end of a sleeve 53 is opened, the user reaches into the space defined between the front of the sleeve and the impermeable surface of the convective apparatus 60, grasps the folded end portion of the first convective device stowed therein, and unfolds the folded end portion out through the opening. This construction interferes minimally with the operation of the convective apparatus 60 since the narrow strip of adhesive bonding occludes only small strips of the permeable surface of the apparatus. At the same time, this construction serves to secure the ends 63 of the convective apparatus 60 against movement with respect to the sleeves 53 of the clinical garment 22.

A multifunction warming device is constituted of a clinical garment and at least one convective apparatus supported on an inside surface of the garment. The convective apparatus is disposed transversely in an upper portion of the clinical garment, running between two sleeves of the clinical garment. With the convective apparatus supported on the inside surface of the garment, the device can be worn by the patient before, during, and after surgery. In preparation for surgery, the convective apparatus is deployed for therapeutic warming while the clinical garment is furled or folded over or around the deployed convective apparatus.

Advantageously, the transverse positioning of the convective apparatus in the upper portion of the clinical garment locates it against the chest of a patient wearing the garment, in proper orientation with the patient's arms and upper chest, and permits it to be deployed and used on the patient's upper body during and after surgery without reorientation of the clinical garment on the patient, removal of the clinical garment from the patient, or removal of the convective apparatus from the gown.

Although the invention has been described with reference to the presently preferred embodiment, it should be understood that various modifications can be made without departing from the spirit of the invention. Accordingly, the invention is limited only by the following claims.

The invention claimed is:

1. A warming device, comprising:
   a clinical garment having an inside surface and an upper portion with opposing sleeves;
   an upper body convective apparatus attached to the inside surface in the upper portion;
   the upper body convective apparatus disposed transversely across the upper portion, along the sleeves;
   at least one inlet port in the upper body convective apparatus; and
   a lower edge on the upper body convective apparatus and an attachment mechanism along the lower edge;
   wherein:
   the upper body convective apparatus includes two laterally-extending sides, each side disposed in a folded configuration in a respective sleeve;
   each sleeve includes an inside cuff retaining a side in the folded configuration, and one or more lines of perforation near the cuff for being opened to provide access through the end of the sleeve to the side in the folded configuration; and,
   each side includes an end of the upper body convective apparatus, and each side being extendable from the folded configuration to an unfolded configuration in which the respective end extends outwardly from the clinical garment.

2. The warming device of claim 1, further including means in each sleeve for releasably retaining a side in the folded configuration in the sleeve.

3. The warming device of claim 2, each side including an end of the upper body convective apparatus, and each side being extendable from the folded configuration to an unfolded configuration in which the end extends outwardly from the clinical garment.

4. The warming device of claim 1, wherein the upper body convective apparatus includes perforation lines extending transversely across each side to enable the separation of the ends from the convective apparatus.

5. A warming device, comprising:
   a clinical garment having an inside surface and an upper portion with opposing sleeves:
   an upper body convective apparatus attached to the inside surface in the upper portion;
   the upper body convective apparatus disposed transversely across the upper portion, along the sleeves;
   at least one inlet port in the upper body convective apparatus; and
   a head drape adjacent the upper surface, in the upper portion;
   wherein:
   the convective apparatus includes two laterally-extending sides, each side disposed in a folded configuration in a respective sleeve;
   each sleeve includes an inside cuff retaining a side in the folded configuration, and one or more lines of perforation near the cuff for being opened to provide access through the end of the sleeve to the side in the folded configuration; and,
   each side includes an end of the convective apparatus, and each side being extendable from the folded configuration to an unfolded configuration in which the respective end extends outwardly from the clinical garment.

6. A warming device, comprising:
   a clinical garment having an inside surface and an upper portion with opposing sleeves:
   an upper body convective apparatus attached to the inside surface in the upper portion;
   the upper body convective apparatus disposed transversely across the upper portion, along the sleeves;
   the upper body convective apparatus including two laterally-extending sides, each side disposed in a folded configuration in a respective sleeve, each side including an end of the convective apparatus, and each side being extendable from the folded configuration to an unfolded configuration in which the end extends outwardly from the clinical garment;
   means in each sleeve for releasably retaining a side in the folded configuration in the sleeve;
   at least one inlet port in the upper body convective apparatus; and
   a head drape adjacent the upper surface, in the upper portion.

7. The warming device of claim 6, wherein the convective apparatus includes perforation lines extending transversely across each side to enable the separation of the ends from the convective apparatus.

\* \* \* \* \*

UNITED STATES PATENT AND TRADEMARK OFFICE
CERTIFICATE OF CORRECTION

PATENT NO. : 8,313,519 B2  
APPLICATION NO. : 12/927800  
DATED : November 20, 2012  
INVENTOR(S) : Thomas P Anderson Page 1 of 1

It is certified that error appears in the above-identified patent and that said Letters Patent is hereby corrected as shown below:

Title Page, Column 2
U.S. Patent Documents, line 1 - Delete "9/1950" and insert -- 6/1950 --, therefore.

Signed and Sealed this
Twenty-fifth Day of June, 2013

Teresa Stanek Rea
*Acting Director of the United States Patent and Trademark Office*